United States Patent [19]
Henderson

[11] Patent Number: 5,357,202
[45] Date of Patent: Oct. 18, 1994

[54] PLURAL ELECTRODE METHOD FOR MEASURING SUBSURFACE CHANGES IN CONDUCTIVITY AS AN INDICATION OF FLUID MIGRATION

[76] Inventor: Michael E. Henderson, 5400 Equity Ave., Ste. B, Reno, Nev. 89502

[21] Appl. No.: 810,332

[22] Filed: Dec. 19, 1991

[51] Int. Cl.$^5$ .................. G01V 3/02; G01M 3/16; G01N 27/04; G01R 27/08
[52] U.S. Cl. .................. 324/557; 324/357; 324/715; 340/605; 405/54
[58] Field of Search ............... 324/347, 357, 557, 559, 324/693, 694, 713, 715; 340/604, 605; 73/40.5 R, 49.2; 405/54

[56] References Cited

U.S. PATENT DOCUMENTS

| | | | |
|---|---|---|---|
| 3,319,158 | 5/1967 | McDoulett et al. | 324/357 |
| 3,383,863 | 5/1968 | Berry | |
| 4,166,244 | 8/1979 | Woods et al. | |
| 4,296,379 | 10/1981 | Yoshizumi | 324/357 |
| 4,404,516 | 9/1983 | Johnson, Jr. | |
| 4,467,283 | 8/1984 | Owen et al. | 324/357 X |
| 4,644,354 | 2/1987 | Kidd | |
| 4,752,881 | 6/1988 | Griffiths et al. | 324/347 X |
| 4,905,210 | 2/1990 | Owen | 367/128 |
| 4,947,470 | 8/1990 | Darilek | 324/557 |
| 4,959,639 | 9/1990 | Benson | 340/618 |

Primary Examiner—Gerard R. Strecker
Attorney, Agent, or Firm—Bernhard Kreten

[57] ABSTRACT

A method and apparatus for monitoring and locating the presence of fluids beyond a containment vessel. A multiplicity of plates having conductive affinity are strategically oriented adjacent the area of liquid storage and periodic surveillance relying on conductivity of the substrate within which the electrodes have been placed are made such that disturbances in the conductivity correlates with migration of fluid being contained. The method and apparatus may be utilized to detect migration of salinated fluids into a region where previously less salination existed.

7 Claims, 3 Drawing Sheets

PLURAL ELECTRODE METHOD FOR MEASURING SUBSURFACE CHANGES IN CONDUCTIVITY AS AN INDICATION OF FLUID MIGRATION

FIELD OF THE INVENTION

This invention relates generally to detecting and locating leaks in liquid containment systems.

BACKGROUND OF THE INVENTION

Containing materials in a specified area is a concern in many industrial enterprises. One of the more conspicuous manifestations of containment includes the sequestration of hazardous waste materials. Should such materials escape from the containment facility in which they are impounded, substantial harm could result, both ecologically and economically. To remedy this potential problem, more responsive techniques for detecting leakage from such facilities are needed.

Difficulties that have arisen with regard to leak detection include, inter alia, variations in one or more qualitative characteristics of the material sought to be contained. This makes characteristic specific sensor calibration critical. Another problem is the containment facility can leak from any containment surface or edge and the composition of the container may have to vary because of the material to be contained. Moreover, conditions in the ground surrounding the facility may not necessarily be constant. Thus, monitoring the facility for leakage can be a very resource intensive effort. Various schemes have been offered for remedying one or some of these difficulties in the past. However, the problems persist, and a better leakage detection system is still a highly sought after commodity.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| INVENTOR | PATENT NO. | ISSUE DATE |
| --- | --- | --- |
| Berry, J. B. | 3,383,863 | May 21, 1968 |
| Woods, et al. | 4,166,244 | August 28, 1979 |
| Johnson, Jr. | 4,404,516 | September 13, 1983 |
| Kidd | 4,644,354 | February 17, 1987 |
| Owen | 4,905,210 | February 27, 1990 |
| Darilek | 4,947,470 | August 7, 1990 |
| Benson | 4,959,639 | September 25, 1990 |

The patent to Berry teaches the use of a leak detector especially for ponds, tanks or pit liners where the leak is located by a change in electrical resistance around two sets of wires disposed underneath the liner and separated by some previous insulating media. In one form of the invention, liquid from a cavity seeps through a normally impervious coat or liner through a leak such that it will dampen the previous insulating material thus altering the electrical resistance between wires. One limitation of this resistance measuring method is that it has difficulty discerning other present subjacent liquids from those contained in the impoundment. Another limitation is that once a leak does occur, such material may persist in the previous insulating media such that future leaks may not be detected. Another limitation is that only point sources are utilized rather then field sources, limiting this device to leak detection without determining the leak's location. A further limitation is that the relatively fragile bare wires used are subject to potential corrosive and deleterious exposure to material such that these essential wires may be permanently destroyed.

Alternatively, the patent to Woods, et al. teaches the use of an electric field produced by application of current to a metallic reference ring surrounding a tank and a metallic portion of that tank. Leaks from the tank are detected by potential changes in the field as are measured between electrodes placed within the field and the tank. A limitation of this potential variation device is that it is slow, if not incapable in some cases, to detect a leak from the bottom of a tank as opposed to the sides of a tank. A further limitation is that in the form presented, physical attachment to a metallic portion of the tank is required. For applications that do not include a metallic tank attachment, a problem arises.

Likewise, the patent to Johnson teaches the use of a network of electrically conductive wires placed under a reservoir wherein the wires are constructed so that point source only not field source chemicals escaping through a leak will corrode the wires or alternatively degrade the insulation around the wires thereby causing a change in the electrical properties of the wire. One limitation of this system is that should a leak occur, future leak detection may be impossible, due to the necessity of corroding the means of discovering the leak. Another limitation of this system is that it requires actual physical contact of the leaking material and the detecting medium. If the leak is shallow, or if the leak happens to pass between the wires, as opposed to over the wires, the leak will not be detected. A further limitation is that only a point source is utilized as opposed to a field source.

The patent to Kidd teaches the use of an apparatus for detecting the presence of fluid comprised of a sensing means buried on either side of a tank. In particular, the apparatus will indicate whether the condition next to the tank is dry, or whether a polar or non-polar liquid is present. An important limitation of this apparatus is its failure to detect a leak that might occur at the bottom of the tank and continue in a downward direction without ever being detected by the sensing devices next to the tank. Another limitation of the apparatus is that its application has been tailored to predominantly support the peculiarities of a service station environment.

Another patent, issued to Owen, teaches the use of a boat and radio transmitter combination to locate a leak in a liquid impoundment. By use of the radio transmitter the location of the boat can be determined when it detects a leak. A clear limitation of this system would involve the use of a corrosive liquid in the impoundment. Such a liquid would corrode the boat and eventually require its replacement. A further limitation of this system is that radio waves are subject to a myriad of interference problems. Should interference occur, it could lead to leaks either not being detected or being misdetected. Yet another limitation of the system is that when a leak is detected, the migration of the leak cannot be monitored, making remedial efforts far more difficult.

The patent to Darilek teaches the use of an array of electric or magnetic field detectors which are placed on one side of the liner of an impoundment. A voltage is impressed across the liner and the impounded material such that when a leak occurs, a current flows through the leak, creating an electrical field and a magnetic field around the leak whose source can be located geometrically. One limitation of this apparatus is the requirement of locating a voltage impressing electrode in the material impounded. It should be noted that if the impounded material were highly corrosive, the electrode would degrade and need eventual replacement. A further limitation is that if a leak is detected, that leak's further migration cannot be monitored by this apparatus, making remedial measures more difficult.

The Benson patent teaches the use of a flexible rod and sleeve assembly to detect the presence of leaking petroleum. The apparatus detects leaking petroleum on its way toward the water table by being constructed of a material which when contacted by petroleum (but not water) will erode and cause the sleeve to move upward activating an alarm. A clear limitation of this assembly is that the material it is intended or able to detect leaks for is petroleum (or other hydrocarbon materials). This very narrowly tailored invention is designed to detect but one very specific type of leak.

SUMMARY OF THE INVENTION

Minerals, rocks, and soil, in different measure, can conduct electricity. The capability of soil or rock material to be effective or ineffective conductors is influenced by characteristics such as particle composition, density, the degree of pore space saturation and the chemical composition of any interstitial fluid (fluid in the spaces between the particles).

A leak from a waste or liquid impoundment facility consists of either conductive or non-conductive fluid which changes the electrical resistivity of material with which it contacts. Liquid leaking through a geomembrane (e.g. plastic liner) will soak the subgrade beneath. Electricity will then pass through these soils with a greater or lesser ease than before the leak occurred. Regularly measuring the difference in resistivity—or its inverse, conductivity—will allow comparisons of the current data with the average to date. Large differences occur and continue to change in magnitude as a leak progresses. By monitoring the locality of such resistivity changes, any leakage from a system will not merely be detected, but also pin-pointed to a particular spatial location.

Unfortunately, resistivity (or conductivity) cannot be measured directly. However, it can be computed if other quantities are measured. These quantities may include the intensity of the current injected into the medium and the magnitude of the potential/voltage established between measurement electrodes. These quantities depend on the geometry of the electric field, the nature of the soils and interstitial fluids, and the method selected to measure the quantities.

The present invention contemplates converting the measured potential to a conductivity value, then stores that value along with the spatial coordinates of the sampling station in a unique file. A computer program then compares the calculated values with the previous statistical average for each station and creates a file that represents the calculated offset (difference) of the current data from the previous average. The program then calculates a new average and stores the values and adds the information to an archive to preserve each individual measured value. The result is an ASCII file (in standardized computer code) that contains values for the position and conductivity of each measuring station in the electrode grid and another file with the offset of the current values from a statistical mean.

Thus, an apparatus is provided by which a leak from a storage facility may be first quickly detected and second pin-pointed by means of monitoring the conductivity of the subjacent soil. The apparatus includes an array of electrodes preferably arranged to be harnessed in groups of four. The electrodes produce a field by which its potential and current, and thus resistivity may be measured. When a leak occurs, the conductivity of the soil increases or decreases depending on the conductivity of the fluid leaking so that the apparatus will detect and locate that leak.

An alternative use of this apparatus is in detecting the migration of salinated water into existing previously-fresh-water aquifers, or other solutions with distinctly different resistivity from the background such as with unsaturated flow monitoring associated with contaminant plumes. The electrodes sense reduced resistivity due to the lower resistance of salt water compared to fresh water.

OBJECTS OF THE INVENTION

A primary object of the present invention is to provide a novel and useful leak detector and locator.

A further object of the present invention is to provide a device as characterized above which detects leaks emanating from a tank, pipe or any other storage or impoundment facility.

A further object of the present invention is to provide a device as characterized above which locates and monitors the migration of leaks from an impoundment facility.

A further object of the present invention is to provide a device as characterized above which detects relatively small leaks in a relatively small area.

A further object of the present invention is to provide a device as characterized above which detects leaks by means of a system completely external to the impoundment facility.

A further object of the present invention is to provide a device as characterized above which detects leaks regardless of prevailing or changing soil conditions.

A further object of the present invention is to provide a device as characterized above which detects leakage of both conductive and non-conductive materials.

A further object of the present invention is to provide a device as characterized above which determines the salinity of an aquifer in a region surrounding a water well.

Viewed from a first vantage point, it is an object of the present invention to provide a device as characterized above wherein the leak detection system is operated by an automated method.

Viewed from a second vantage point, it is an object of the present invention to provide a device as characterized above wherein an automated system provides the user with an easy to read graphical printout of the current or base soil conditions around and below an impoundment facility.

Viewed from a third vantage point, it is an object of the present invention to provide an apparatus for detecting and locating a leak in an impoundment, comprising, in combination: a soil substrate underlying and conformed to mirror the impoundment, a plurality of sensing means attuned to variation in potential differences in an individual sensing means and with respect to another sensing means, a current supply connected between the sensing means such that an electric field is established between the sensing means when the current supply is energized, wherein the sensing means is oriented in the soil substrate, and the impoundment is provided with a substance, which when admitted to the soil substrate alters the potential difference of the sensing means, and monitoring means for denoting the change in the potential difference.

Viewed from a fourth vantage point, it is an object of the present invention to provide a method for monitoring the presence and migratory proclivity of a fluid in a medium having substantially constant conductivity, the method including the steps of: installing electrodes in a soil substrate conformed to mirror an overlying impoundment such that the electrodes have directional sensitivity; initializing the electrodes with respect to the characteristics of the medium to obtain a baseline measurement; measuring the potential difference between the electrodes at selected time intervals; archiving measurements obtained at the selected time intervals for future reference as to prevailing conditions; comparing the archived measurements with currently obtained measurements; displaying results of the archived measurements; and signaling in the presence of an anomalous reading which may be correlative of fluid migration.

Viewed from a fifth vantage point, it is an object of the present invention to provide a system for monitoring the presence of a leak in an impoundment, comprising, a plurality of electrodes, each having directional sensitivity and all mutually oriented with respect to one another such that when a current is impressed on any one pair of electrodes, a potential profile is impressed upon another pair, wherein the electrodes are operatively conditioned by the impoundment such that a leak from the impoundment affects the electrodes, and monitoring means coupled to the electrodes to monitor the potential.

Viewed from a sixth vantage point, it is an object of the present invention to provide a system for monitoring changes in the salinity of portions of an underground aquifer comprising a plurality of electrodes oriented in an array and having directional sensitivity such that when an electric current is impressed on two electrodes of the array a potential difference is imposed between two other electrodes in the array, the electrodes are positioned along a region where salinated water migration is suspected, and wherein the potential difference between the electrodes is calculated and utilized to determine the resistivity of underground soil between the electrodes, whereby when salinated water penetrates soil surrounding the electrodes, the resistivity of the soil is decreased due to the different electrolytic properties of salinated water indicating that salinated water migration is occurring.

These and other objects will be made manifest when considering the following detailed specification when taken in conjunction with the appended drawing figures.

DESCRIPTION OF PREFERRED EMBODIMENTS

Figure 1:
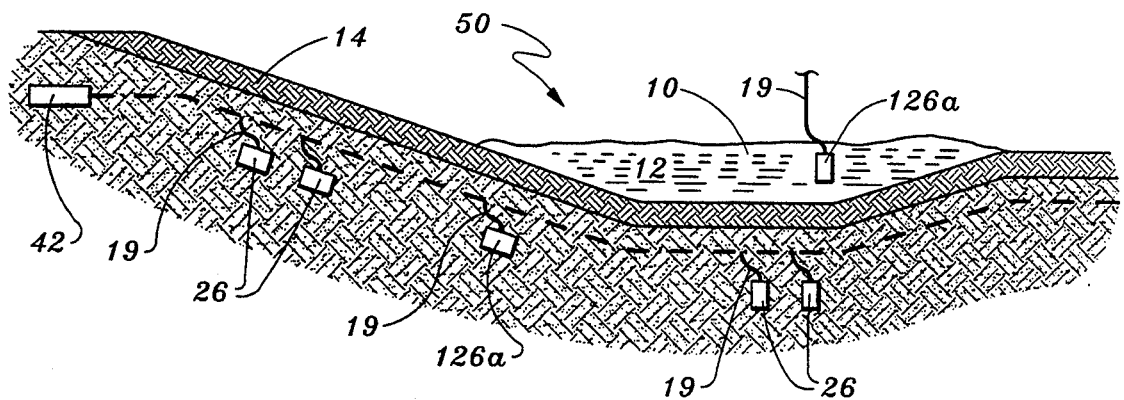
FIG. 1 is a side view depiction of the apparatus according to the present invention in its intended environment.
Figure 6:
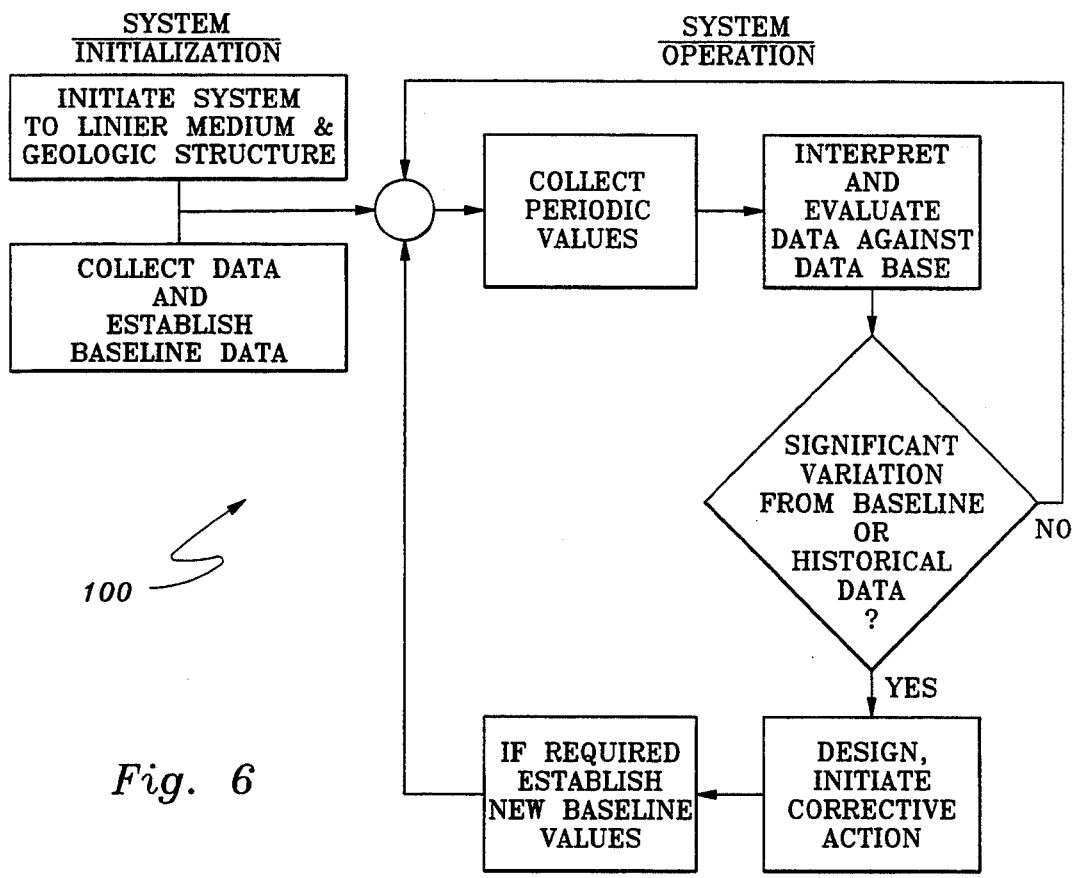
FIG. 6 is a flow chart associated with the utilization of the instant invention, showing its methodology.

Referring to the drawings now wherein like reference numerals refer to like parts throughout the various drawing figures, reference numeral 50 is directed to the leak detector and locator according to the present invention. In essence, the detector 50 includes an array of probes 75 (FIG. 2) deployed below a liner 14 (FIG. 1). These probes 75 are operatively coupled to an analysis system 100, 110 shown in FIGS. 6 and 7. Collectively, this structure produces output in a three dimensional graph which represents either the existence of a leak (FIG. 4) or normal conditions (FIG. 3).

The geometry of the electric field is determined by first the positions of electrodes 26a (FIG. 2) used to inject the current and second, the configuration of the electrodes 26b used to measure the potential. The preferred embodiment uses a permanent electrode grid in an equally spaced rectangular arrangement within the sand or subgrade of the system. Four electrodes 26 in a row are preferred to take a measurement. An outer pair of electrodes 26a is used to inject the current and an inner pair of electrodes 26b measures the potential. The resistivity is computed at a virtual point 29 between the inner electrodes 26b. The virtual point 29 is called a measurement station. The preferred embodiment contemplates electrodes 26 spaced every one hundred feet in a ground liner system. The device manifests sufficient resolution to detect as little as fifty gallons of added liquid and then direct the search for the leak to an area within a fifty foot radius.

Referring now to FIG. 1, one embodiment of the detection system of the present invention is shown which is specifically adapted for use with a solution 12 reservoir. Although the embodiment shown in FIG. 1 is specifically directed to a lined liquid/sludge impoundment, it should be understood that the principles of the invention are applicable to a myriad of applications including, but not limited to: lined landfill cells, hazardous waste site cells, areas where migration of salinated water is suspected, lined water storage facilities, petroleum handling facilities, tank farms, or heap leach facilities.

As depicted in FIG. 1, storage channel 10 has been formed in the soil for the purpose of holding solution 12. Beneath storage channel 10 is geomembrane liner 14. In the event solution leaks from channel 10 through liner 14 and solution 12 permeates beyond geomembrane liner 14, a four-point probe 75 grid located within a leak detection layer 16 of FIG. 1, will register a leak when it occurs. Each four-point probe 75 operates as shown in FIG. 2.

Figure 5:
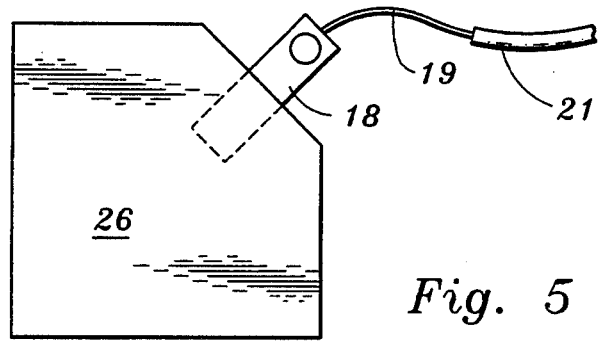
FIG. 5 is a map view of a typical electrode associated with the present invention.

In the preferred embodiment, the four-point probe 75 includes four stainless steel plates 26 also called electrodes 26 depicted in FIG. 5. Each plate 26 is a substantially rectangular construct having two opposing faces with surface areas significantly greater than the thickness of plate 26. Each plate 26 includes three 90° corners and one truncated corner such that a five edged construct is formed. Thus, one corner of a rectangular construct will have been mitered at 45°.

To better facilitate an effectual lead to plate 26, copper tab 18 is coupled to plate 26 at a midpoint of the mitered, truncated corner. Wire 19, formed of sixteen gage multistrand copper wire and covered with a high-density polyethylene jacket 21 rated for direct burial, then connects to plate 26 at copper tab 18. The tab 18 may be electrically coupled to the plate 26 by either embedment, soldering or both.

Figure 2:
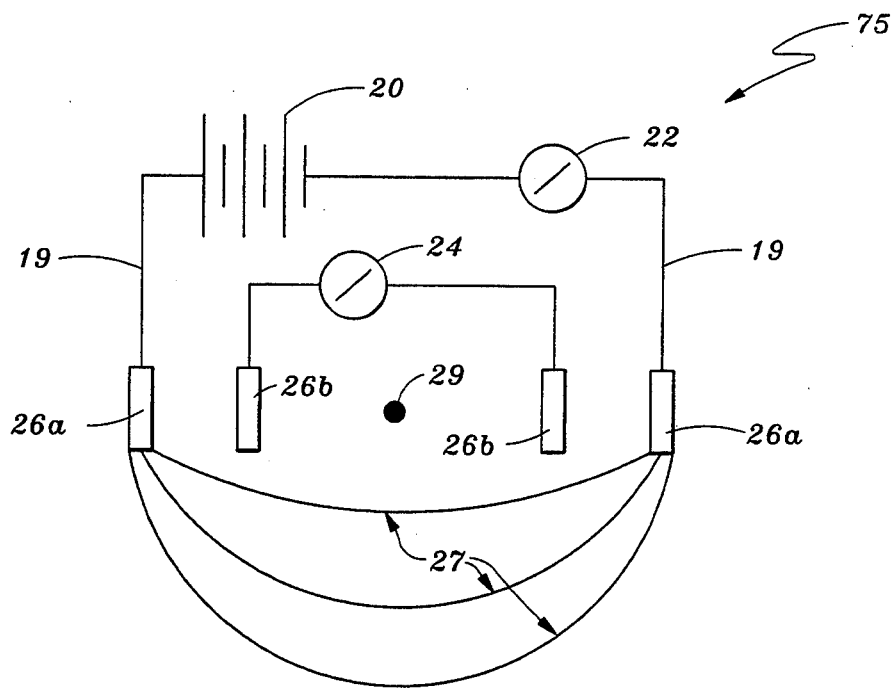
FIG. 2 is a schematic depiction of an electrode array in its operative mode and used as a measurement device.
Figure 3:
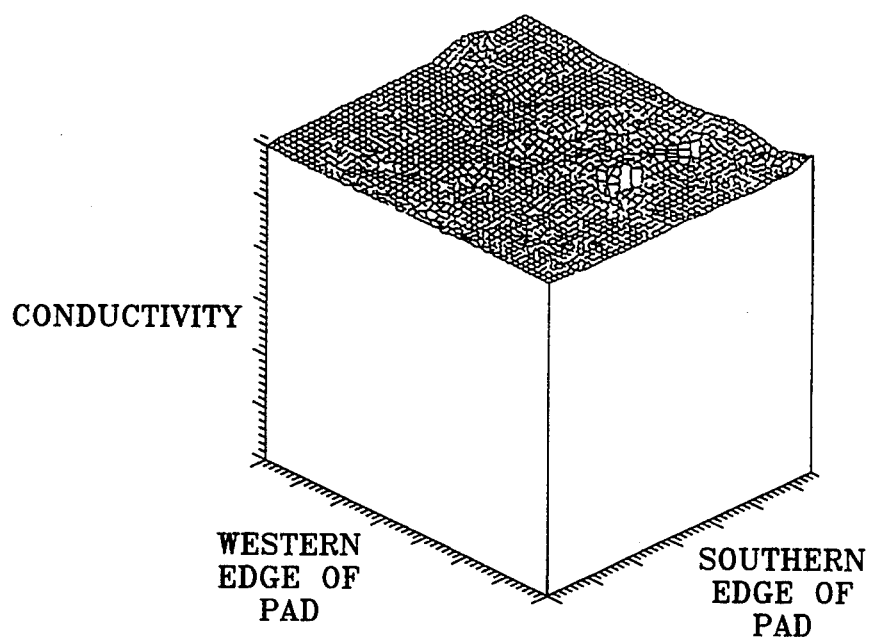
FIG. 3 is a three-dimensional graphic depiction of the area being surveiled according to the present invention.

As depicted in FIG. 2 an opposite end of wire 19 connects to either a power source 20 and current meter 22 or to a voltmeter 24. Each part of tab 18 and bare wire 19 is coated with electrical insulating varnish or equivalent waterproof coating so that no exposed copper exists uncovered.

In particular, as depicted in FIG. 2, when power supply 20 is energized, current flows through wire 19 to "outer" reference electrodes 26a—26a forming potential field 27. By means of current meter 22 connected in series with power supply 20 and reference electrodes 26a—26a, the applied current to the system may thus be readily determined. Further, by connecting voltage meter 24 in parallel across "inner" detection electrodes 26b—26b, the voltage may be readily determined at measurement station 29 (virtual point).

Given the voltage and current, the following equations will then determine the resistivity:

$$Ra = K*V/I$$

where

V is the voltage measured by voltage meter 24
I is the current measured by current meter 22
and constant $$K = 2*\pi*(AB/3)$$

where

AB denotes the distance between each current impressing electrode 26a.

Additionally, in terms of conductance (G), a more understandable quantity in these situations:

$$G = 1/Ra.$$

Although each data point may be determined manually, experience shows that it is more cost effective to have a computer system compile and distill the data into graphical reports. Such a system is depicted logically in FIG. 6 and graphically in FIG. 7. In particular, computer 40 causes analog measurements of voltage and current to be taken for measuring stations 29 in leak detection layer 16 by means of computer controllable switching devices contained in jack panel 42.

In essence, the computer switching moves from one four-point probe 75 to the next, where the next four-point probe 75 consists of three electrodes 26 from the first four-point probe 75 and one new electrode 26 in the row such that each measuring station 29 consists of a four-point probe 75 as depicted in FIG. 2. Analog signals, derived therefrom, are converted to digital signals by means of analog-to-digital converter (ADC) 44 such that computer 40 may store and compile that digital signal so that it may be compared to previously taken baseline data sets created during initialization of the electrodes with respect to the pre-existing characteristics of the medium or displayed as raw data in terms of conductivity.

As mentioned infra "outer" electrodes 26a and "inner" electrodes 26b operate in concert to provide the leak surveillance. In actuality, the terms "inner" and "outer" are relative since the device 50 typically has a multiplicity of electrodes 26 well in excess of four which are oriented in a matrix 80 defining an R by C array where R is the number of rows and C is the number of columns. One electrode plate 26 is oriented at the intersection of each row and column. For example, and with reference to FIG. 7, a lined impoundment electric grid defines the leak detection layer 16. This matrix 80 or grid 80 is operatively coupled to the jack panel 42. Each of the "nodes" in the electric grid 80 is an ideal site for the disposition therewithin of one electrode plate 26. The surveillance and sampling involves sampling four electrodes 26 at a time such that the "outer" electrodes 26a impress thereon a current and the "inner" electrodes 26b monitor a voltage associated therewith.

Figure 7:
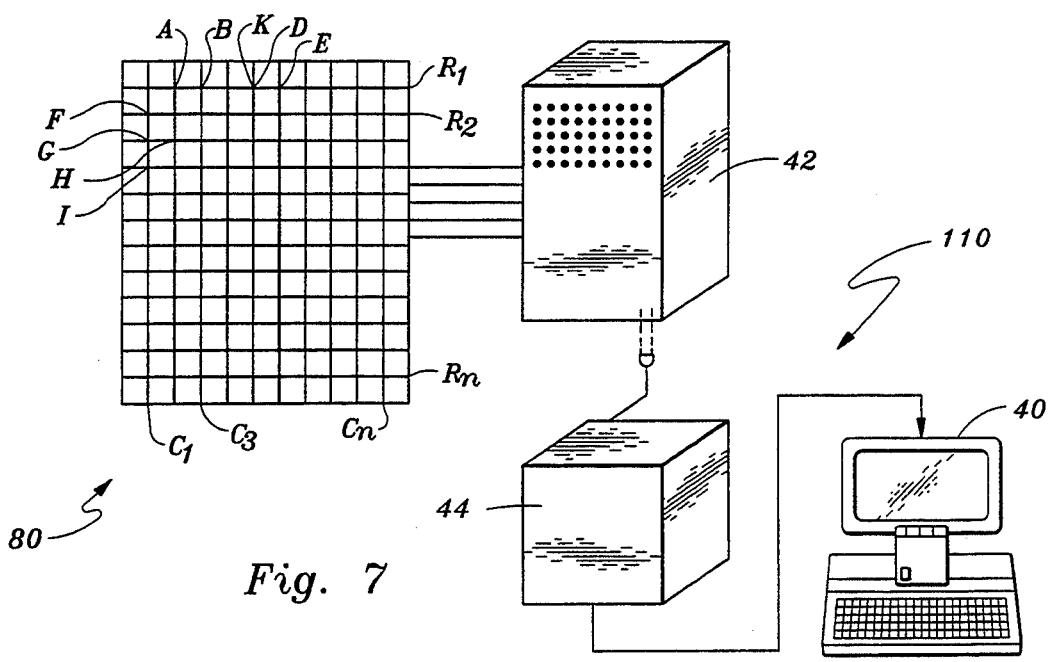
FIG. 7 is a further conceptual flow diagram associated with the present invention.

After one reading a subsequent reading again relying on four electrodes 26 is made, but one electrode 26 from the previous sample will have been dropped while another "new" electrode 26 will have been added. Therefore, as shown in FIG. 7, and by way of example, a first reading from grid 80 within layer 16 may be taken using plates 26 located at nodes A, B, K, D. A second reading may be taken by dropping electrode A and adding electrode E. Thus, the second reading would be comprised of electrodes B, K, D, E. In this example, the measurements are iteratively taken along one row R in the R by C array. Alternatively, the measurement could have been taken along a column such as column $C_2$. In this event, a first reading may utilize electrodes A, F, G, H. A successive reading may thereafter utilize electrodes F, G, H, I and so on.

In practice, it is intuitively proper to have all of the electrodes 26 substantially parallel one to the other although this is not necessary so long as proper initialization procedures are effected. Thus, mutual parallelism between adjacent or even all electrodes 26 is not necessary according to the instant invention, thereby making installation parameters less critical. The initialization proceeding would therefore become more important for standardization. Experimental data has shown that the field that emanates from any electrode conductive plate 26 is substantially spherical with minor edge effects adjacent the edges of the electrode 26. The initialization proceeding also initializes the electrodes with respect to the pre-existing characteristics of the medium to obtain a baseline measurement of potential difference between the electrodes representative of medium conductivity.

In an alternative embodiment (FIG. 1), a current source electrode 126a is located above the liner 14 within the solution 12. This current source electrode 126a replaces one of the electrodes 26a of the four-point probe 75. Thus, the grid of electrodes 26a, 26b is switched as a group of three electrodes rather then a group of four electrodes 26a, 26b. The three electrodes 26a, 26b consist of two voltage measuring electrodes 26b and one current sink electrode 26a.

Alternatively, the current sink electrode 26a may be replaced with a stationery current sink electrode 126a located above or below the liner 14. In this embodiment, the current field 27 is kept stationery and only the voltage measuring electrodes 26b are switched through the grid 16.

Figure 4:
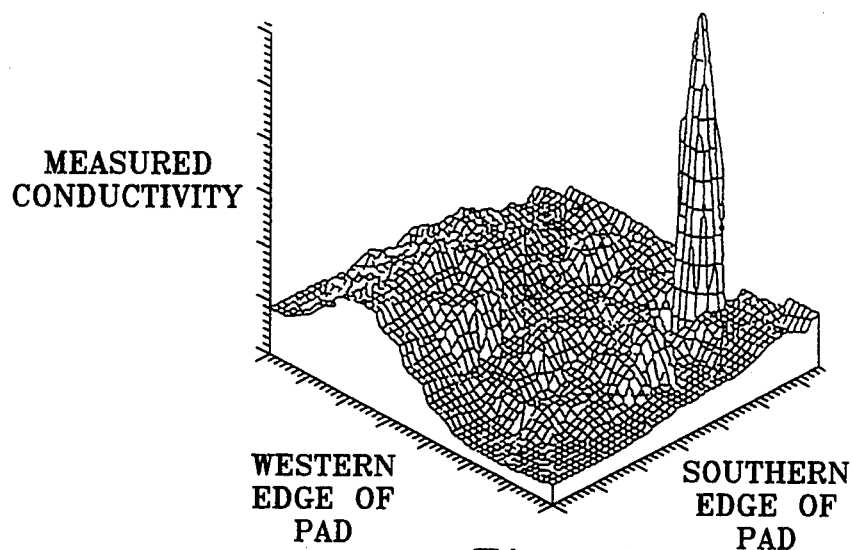
FIG. 4 is a view similar to FIG. 3 but showing the three-dimensional depiction after introduction of 200 gallons of solution in the lower right-hand portion of the FIG. 3 depiction.

To further assist a human user, with the aid of a graphical statistical interpretation program, the data may be displayed topographically as in FIG. 3 where a three dimensional plot consisting of the spatial coordinates of the measuring station on the grid 16 and the conductivity, G, measured at that station is shown. Further, should a leak be present, a topographical display will readily alert the viewer of such data to a problem as can be seen in FIG. 4, where the unusual peak depicts the location of a leak consisting of a material whose conductivity (G) is greater than the surrounding medium. Using the above described method of detection on a regular and daily basis allows additional analysis to be accomplished such as determination of random, periodic, seasonal and cyclic variations in the measured data. That is, compilation of soil conductivity data during a storm or during a particular season will allow a more accurate assessment of the measured data during a repeated rain or during a season in which soil conditions may change by comparing the most recent measurement to such archived conditions in existence at the time of the measurement, appropriate comparisons can be made between the most recent measurement and archived measurements indexed with similar prevailing conditions. The system can thus determine more accurately whether a leak has indeed occurred or whether instead, the soil conductivity (G) has changed due to the weather or seasonal changes. When a conductivity measurement has a significant variation from baseline measurements and the archived measurements, which may be correlative of fluid migration, an appropriate signal can be generated.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A method for monitoring the presence and migratory proclivity of a fluid in a medium having discernable conductivity, the method including the steps of:
   installing a plurality of electrodes embedded permanently within a soil substrate conformed to mirror an overlying impoundment;
   initializing said electrodes with respect to the pre-existing characteristics of the medium to obtain a baseline measurement of potential difference between the electrodes representative of medium conductivity;
   applying a current to the medium at selected time intervals;
   measuring the potential difference between said electrodes as representative of conductivity at said selected time intervals;
   archiving the measurements obtained at the selected time intervals during the measuring step for future reference, each of said measurements indexed with reference to prevailing conditions in existence at the time of the measurements;
   repeating said current applying and measuring steps at a later time to obtain a current measure of the potential difference under currently existing prevailing conditions;
   comparing the currently obtained measurements to archived measurements archived during prevailing conditions in existence which are similar to the currently existing prevailing conditions to detect changes in potential difference between the currently obtained measurements and the archived measurements;
   displaying results of the changes detected during said comparing step indicating a difference between current measurements and archived measurements indexed with similar prevailing conditions;
   and signaling in the presence of a measurement having a significant variation from the baseline measurements and the archived measurements which may be correlative of fluid migration.

2. The method of claim 1 including:
   orienting multiple electrodes in an array defining rows and columns,
   grouping together certain electrodes for measuring,
   and thereafter selecting an additional electrode for measuring while omitting a previously grouped electrode thereby iteratively moving along the electrodes in the soil substrate.

3. The method of claim 2 including:
   grouping four electrodes,
   applying a current to two of the electrodes which are outboard relative to two remaining inboard electrodes, and
   measuring the potential impressed upon the two inboard electrodes.

4. The method of claim 3 further including fashioning the electrodes as substantially flat plates and orienting the plates in mutual parallelism.

5. The method of claim 2 including:
   grouping three electrodes from among the plurality of electrodes within the soil substrate,
   positioning a current supply electrode above the impoundment,
   applying a current between the current supply electrode and one of the electrodes from the group of three electrodes; and
   measuring a potential difference between two electrodes from the group of three electrodes.

6. A method for monitoring the presence and migratory proclivity of a fluid in a medium having discernable conductivity, the method including the steps of:
   installing a plurality of electrodes proximate to an area of expected fluid migration;
   initializing said electrodes with respect to the pre-existing characteristics of the medium to obtain a baseline measurement of potential difference between the electrodes representative of medium conductivity;
   applying a current to the medium at selected time intervals;
   measuring the potential difference between said electrodes as representative of conductivity at said selected time intervals;
   archiving the measurements obtained at the selected time intervals during the measuring step for future reference, each of said measurements indexed with reference to prevailing conditions in existence at the time of the measurements;
   repeating said current applying and measuring steps at a later time to obtain a current measure of the potential difference under currently existing prevailing conditions;

comparing the currently obtained measurements to archived measurements archived during prevailing conditions in existence which are similar to the currently existing prevailing conditions to detect changes in potential difference between the currently obtained measurements and the archived measurements;

displaying results of the changes detected during said comparing step indicating a difference between current measurements and archived measurements indexed with similar prevailing conditions;

and signaling in the presence of a measurement having a significant variation from the baseline measurements and the archived measurements which may be correlative of fluid migration.

7. The method of claim 6 including installing one electrode in a fluid impoundment contacting the fluid with the one electrode, installing a plurality of similar electrode adjacent the impoundment, and coupling the one electrode with some of the plurality of similar electrodes.

* * * * *